United States Patent [19]

Conley et al.

[11] Patent Number: 4,731,480

[45] Date of Patent: Mar. 15, 1988

[54] PROCESS FOR PREPARING 2-ACYL-3,4-DIALKOXYANILINES

[75] Inventors: Richard A. Conley, Annandale; Donald L. Barton, Frenchtown, both of N.J.

[73] Assignee: Ortho Pharmaceutical Corporation, Raritan, N.J.

[21] Appl. No.: 760,003

[22] Filed: Jul. 29, 1985

[51] Int. Cl.[4] ............................................ C07C 103/38
[52] U.S. Cl. .................................... 564/223; 544/90; 562/455; 564/143; 564/443
[58] Field of Search ................................ 564/443, 223

[56] References Cited

U.S. PATENT DOCUMENTS

| | | | |
|---|---|---|---|
| 2,987,546 | 6/1951 | Muller | 564/223 |
| 3,405,126 | 10/1968 | Ichibagase et al. | 564/223 X |
| 3,634,455 | 1/1972 | Lednicer | 564/223 X |
| 4,453,004 | 6/1984 | Nelson | 564/223 X |
| 4,453,018 | 6/1984 | Nelson | 564/223 X |
| 4,555,571 | 11/1985 | Bandurco et al. | 564/443 X |
| 4,556,739 | 12/1988 | Kanojia et al. | 564/443 |

*Primary Examiner*—Robert V. Hines
*Attorney, Agent, or Firm*—Benjamin F. Lambert

[57] ABSTRACT

A process for preparing 2-acyl-3,4-dialkoxyanilines is described. The 2-acyl-3,4-dialkoxyanilines are useful intermediates in the preparation of 5,6-dialkoxy-4-alkyl-2(1H)-quinazolinones. The substituted quinazolinones are active as cardiotonic agents.

2 Claims, No Drawings

PROCESS FOR PREPARING 2-ACYL-3,4-DIALKOXYANILINES

The present invention relates to a method of preparing 2-acyl-3,4-dialkoxyanilines.

The 2-acyl-3,4-dialkoxyanilines which are the subject of this invention have the following formula:

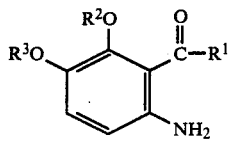

wherein $R_1$, $R_2$ and $R_3$ are lower alkyl having 1-5 carbon atoms and $R_2$ and $R_3$ when taken together are methylenedioxy.

The preparation of the 2-acyl-3,4-dialkoxyanilines is illustrated by the following schematic diagram:

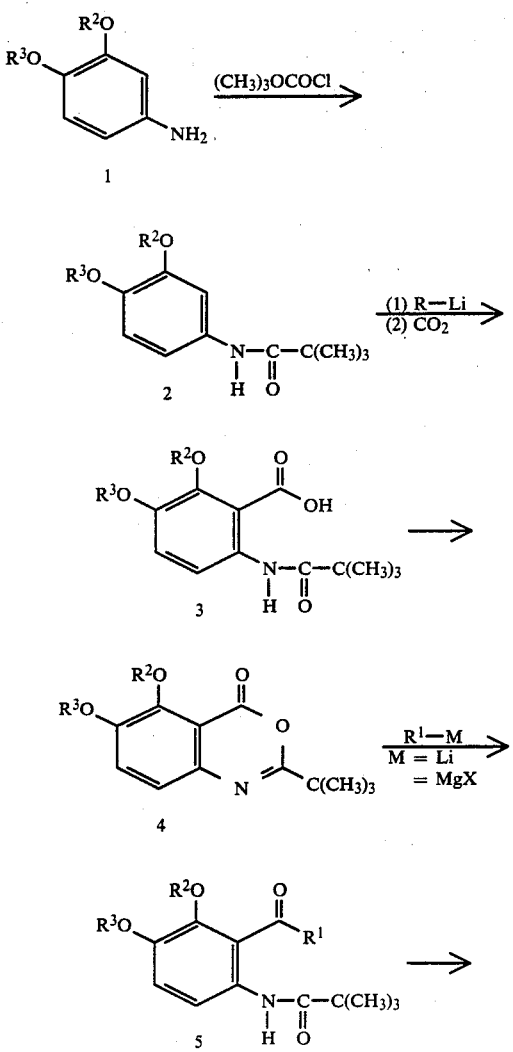

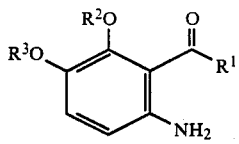

wherein $R_1$, $R_2$ and $R_3$ are lower alkyl having 1-5 carbon atoms, R is n-butyl, s-butyl or t-butyl and X is halo such as chloro or bromo.

In each of the steps in the process, the products are isolated where indicated and characterized by techniques known to those skilled in the art.

As can be seen from the above diagram, the first step in the synthesis of the 2-acyl-3,4-dialkoxyanilines involves the reaction of a 3,4-dialkoxyaniline (1) with a pivalic acid halide or anhydride such as pivaloyl chloride, pivaloyl bromide, pivaloyl fluoride, or pivalic anhydride to form a 3',4'-dialkoxy-2,2-dialkylpropioanilide (2). The reaction is carried out in a suitable solvent, such as, for example, methylene chloride or tetrahydrofuran, in the presence of a suitable base such as sodium hydroxide, potassium hydroxide or triethylamine. The reaction may be carried out at temperatures between 5° C. and room temperature. The anilide (2) is then reacted with an organolithium reagent such as, for example, n-butyllithium, s-butyllithium or t-butyllithium, to form in situ the corresponding dilithio intermediate which is then reacted with carbon dioxide to give the corresponding 2'-carboxy-3',4'-dialkoxy-2,2-dialkylpropioanilide (3). The reaction is carried out in a suitable solvent such as tetrahydrofuran, dioxane or diethyl ether, for example, at a temperature ranging from 0° C. to room temperature. The acid (3) is then cyclized with an acid anhydride such as acetic anhydride, propionic anhydride or butyric anhydride, for example, in a suitable solvent such as acetic acid, propionic acid or butyric acid, to form the 2-alkyl-5,6-dialkoxy-1,3-benzoxazin-4-one (4). The reaction is carried out preferably at the reflux temperature of the solvent mixture. Treatment of the 1,3-benzoxazin-4-one (4) with an organometallic reagent such as an alkyllithium reagent, for example, methyllithium, or an alkylmagnesium halide such as, for example, methylmagnesium bromide, gives the 2'-acyl-3',4'dialkoxy-2,2-dialkylpropioanilide (5). The reaction is carried out in a suitable solvent, such as tetrahydrofuran at a temperature between −5° C. and room temperature. Acid hydrolysis of the anilide (5) gives the 2-acyl-3,4-dialkoxyaniline (6). Suitable acids which can be employed include sulfuric acid and hydrochloric acid.

Where not otherwise indicated in the specification, lower alkyl shall mean an alkyl group containing from 1-4 carbon atoms.

The 2-acyl-3,4-dialkoxyanilines are useful as intermediates in the preparation of the 5,6-dialkoxy-4-alkyl-2(1H)-quinazolinones which are the subject of U.S. Pat. No. 4,490,374, the pertinent subject matter of which is incorporated herein by reference. The 5,6-dialkoxy-4-alkyl-2(1H)-quinazolinones are useful as cardiotonic agents.

The process of this invention eliminates the regioisomer problems associated with the preparation of the 5,6-dialkoxy-4-alkyl-2(1H)-quinazolinones disclosed in U.S. Pat. No. 4,490,374, while shortening the overall synthesis. Some of the intermediates prepared in the synthesis of the 2-acyl-3,4-dialkoxyanilines are novel compounds and as such are part of the present invention.

All of the starting materials employed in the process are either known materials or can be readily made from known materials by one skilled in the art.

The following examples describe the invention in greater particularity and are intended to be a way of illustrating but not limiting the invention.

EXAMPLE 1

3',4'-Dimethoxy-2,2-dimethylpropioanilide

A solution of 368 g (2.4 mol) of 3,4-dimethoxyaniline in 1400 mL of methylene chloride was prepared and treated with Darco at 25° C. for 20 minutes. After filtering through a Hyflo bed, 1320 mL of 2N sodium hydroxide was added and the reaction mixture was cooled to 10° C. Pivaloyl chloride (2.4 mol—296 mL) was added over 1 hour and the reaction mixture was then stirred for an additional hour at room temperature. The methylene chloride layer was separated, dried with magnesium sulfate, and Darco treated. The resultant methylene chloride solution was heated to reflux (45° C.) and 1500 mL of heptane was added. The reaction was then cooled to 30° C. and 1000 mL of 10:90 methylene chloride/heptane was added with cooling to 0° C. Filtration gave 467 g (82%) of the desired product, mp 126°-128° C. NMR (CDCl$_3$) δ 1.30 (s, 9H, C—CH$_3$), 3.83 (s, 3H, OCH$_3$), 3.87 (s, 3H, OCH$_3$), 6.80 (m, 2H, ArH), 7.27 (br s, 1H, NH), 7.42 (m, 1H, ArH).

EXAMPLE 2

2'-Carboxy-3',4'-dimethoxy-2,2-dimethylpropioanilide

A solution of 100 g (0.42 mol) of 3',4'-dimethoxy-2,2-dimethylpropioanilide in 1000 mL of tetrahydrofuran was prepared under a nitrogen atmosphere and cooled to 0° C. A solution of n-butyllithium in hexane or heptane (0.844 mol—538 mL—1.57M) was added and the reaction mixture was then stirred at 0° C. for 1 hour. Carbon dioxide gas was then bubbled in for 0.5 hr and the reaction mixture was then warmed to room temperature. Following dilution with 500 mL of water and acidification to pH 2 with 100 mL of concentrated hydrochloric acid, the layers were separated and the aqueous layer was extracted with 1250 mL of methylene chloride. The combined organic layers were dried over magnesium sulfate, treated with Darco, and evaporated at 80° C. Heptane (500 mL) was added and the solution was cooled to crystallize the product. Filtration gave 95 g (80%) of the desired product, mp 91°-95° C. NMR (CDCl$_3$) δ 1.33 (s, 9H, C—CH$_3$), 3.90 (s, 3H, OCH$_3$), 4.07 (s, 3H, OCH$_3$), 7.13 (d, 1H, J=10 Hz, ArH), 8.52 (d, 1H, J=10 Hz, ArH), 10.87 (br s, 1H, NH or CO$_2$H), 11.25 (br s, 1H, NH or CO$_2$H).

EXAMPLE 3

2-t-Butyl-5,6-dimethoxy-1,3-benzoxazin-4-one

A solution of 14.1 g (50 mmol) of 2'-carboxy-3',4'-dimethoxy-2,2-dimethylpropioanilide in 250 ml of acetic anhydride and 100 ml of acetic acid was refluxed for 2 hr. Rotary evaporation gave 12.7 g (97%) of the desired product as an oil which solidified upon standing. NMR (CDCl$_3$) δ 1.35 (S, 9H, C—CH$_3$), 3.90 (s, 3H, OCH$_3$), 3.95 (s, 3H, OCH$_3$), 7.30 (s, 2H, ArH).

EXAMPLE 4

2'-Acetyl-3',4'-dimethoxy-2,2-dimethylpropioanilide

Under a nitrogen atmosphere, a solution of 12.4 g (47 mmol) of 2-t-butyl-5,6-dimethoxybenzoxazin-4-one in 50 ml of tetrahydrofuran was prepared and cooled to −5° C. A 3.2M solution of methylmagnesium bromide in ethyl ether (36.7 mL—118 mmol) was added slowly while keeping the temperature between 15°-25° C. Stirring was continued at 0° C. for 30 min and then 10 mL of a saturated ammonium chloride solution was added. The reaction mixture was added to 100 mL of ether and 90 mL of saturated ammonium chloride. The ammonium chloride layer was extracted with 2×100 mL of ether and the combined organic layer was then extracted with 2×50 mL of saturated sodium carbonate. The organic layer was dried over sodium sulfate and rotary evaporated to give 12.4 g (94%) of the desired product as an oil which solidified upon standing. NMR (CDCl$_3$) δ 1.28 (s, 9H, C—CH$_3$),

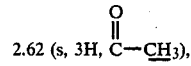
2.62 (s, 3H, C—CH$_3$), 3.88 (s, 6H, O—OH$_3$), 7.02 (d, 1H, J=9 Hz, ArH), 8.07 (d, 1H, J=9 Hz, ArH), 9.88 (s, 1H, NH).

EXAMPLE 5

2-Acetyl-3,4-dimethoxyaniline

A solution of 4.0 g (14 mmol) of 2'-acetyl-3',4'-dimethoxy-2,2-dimethylpropioanilide in 25 ml of 25% sulfuric acid and 25 ml of methanol was prepared and refluxed for 20 hr. The reaction was cooled to room temperature, diluted with 100 mL of water and then extracted with 100 mL of methylene chloride. The aqueous layer was adjusted to pH 9 and extracted with 100 mL of methylene chloride. This methylene chloride solution was dried over sodium sulfate and decolorized with charcoal. Evaporation gave 2.4 g (85%) of the product as a brown solid. NMR (CDCl$_3$) δ 2.60 (s, 3H, C—CH$_3$), 3.80 (s, 3H, OCH$_3$), 3.87 (s, 3H, OCH$_3$), 5.00 (s, 2H, H$_2$), 6.33 (d, 1H, J=8 Hz, ArH), 6.90 (d, 1H, J=8 Hz, ArH).

Anal. Calcd for C$_{10}$H$_{13}$NO$_3$: C, 61.53; H, 6.71; N, 7.18. Found: C, 61.54; H, 6.77; N, 7.12.

Preparation of 5,6-dimethoxy-4-methyl-2(1H)-quinazolinone from a 2-acyl-3,4-dialkoxyaniline 5,6-Dimethoxy-4-methyl-2(1H)-quinazolinone Hydrochloride Hydrate 2-Acetyl-3,4-dimethoxyaniline (15.00 g, 0.077 mole) in acetic acid (375 mL) was treated with potassium isocyanate (15 g) portionwise over 1-3 hours. The mixture was stirred under a nitrogen atmosphere at 25°-35° C. for 16 hours. The precipitate was collected by filtration, washed with water (100 mL) and acetone (100 mL) and air dried to give a solid (12.6 g, 74%). The solid was suspended in water (175 mL), warmed to 70° C. and concentrated hydrochloric acid (175 mL) was added. The temperature was raised to 110° C. until complete solution occurred. Hot filtration, subsequent cooling to 15° C. with stirring and filtration, of the resulting precipitate provided the title compound as yellow crystals. Washing with 6N hydrochloric acid (30 mL) and acetone (120 mL) and drying gave 12.68 g (71%) of the hydrate of 5,6-dimethoxy-4-methyl-2(1H)-quinazolinone hydrochloride, mp 203°–205° C.
What is claimed is:
1. A compound of the formula
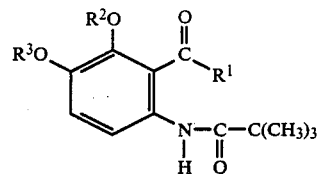
wherein $R_1$, $R_2$ and $R_3$ are lower alkyl.
2. The compound of claim 1 which compound is 2'-acetyl-3',4'-dimethoxy-2,2-dimethyl-propioanilide.
* * * * *